US011628304B2

(12) United States Patent
Govari et al.

(10) Patent No.: US 11,628,304 B2
(45) Date of Patent: Apr. 18, 2023

(54) DETECTION AND MAPPING OF PHRENIC NERVE BY PACING

(71) Applicant: BIOSENSE WEBSTER (ISRAEL) LTD., Yokneam (IL)

(72) Inventors: Assaf Govari, Haifa (IL); Andres Claudio Altmann, Haifa (IL); Israel Zilberman, Yokneam (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 512 days.

(21) Appl. No.: 16/835,617

(22) Filed: Mar. 31, 2020

(65) Prior Publication Data

US 2021/0299453 A1 Sep. 30, 2021

(51) Int. Cl.
*A61N 1/37* (2006.01)
*A61B 18/14* (2006.01)
(Continued)

(52) U.S. Cl.
CPC ........ *A61N 1/3702* (2013.01); *A61B 18/1492* (2013.01); *A61N 1/0587* (2013.01); *A61B 5/062* (2013.01); *A61B 2017/00075* (2013.01); *A61B 2017/00199* (2013.01); *A61B 2018/00351* (2013.01); *A61B 2018/00577* (2013.01);
(Continued)

(58) Field of Classification Search
CPC ................ A61N 1/3702; A61N 1/0587; A61B 18/1492; A61B 5/062; A61B 2017/00075; A61B 2017/00199; A61B 2018/00351; A61B 2018/00577; A61B 2018/00613; A61B 2018/00839; A61B 2018/00898; A61B 2018/00434; A61B 2034/2051; A61B 5/4848; A61B 5/4893; A61B 5/1135; A61B 18/12; A61B 2018/00755
See application file for complete search history.

(56) References Cited

U.S. PATENT DOCUMENTS 5,391,199 A  2/1995  Ben Haim
6,239,724 B1  5/2001  Doron
(Continued)

FOREIGN PATENT DOCUMENTS

WO  WO1996005768 A1  2/1996
WO  WO2018212840 A1  11/2018

OTHER PUBLICATIONS

European Search Report for corresponding EPA No. 21165834.9 dated Aug. 25, 2021.

*Primary Examiner* — Rex R Holmes

(57) ABSTRACT

An apparatus includes an interface and a processor. The interface is configured to receive one or more magnetic-positioning signals from one or more position sensors coupled to one or more body-surface patches attached to a body of a patient, the magnetic-positioning signals indicative of respective positions of the position sensors. The processor is configured to (i) detect an inadvertent stimulation of a phrenic nerve of the patient, which occurs due to cardiac pacing applied by an intra-cardiac electrode in a heart of the patient, (ii) estimate, based on the magnetic-positioning signals, a motion of one or more of the body-surface patches occurring during the detected stimulation of the phrenic nerve, (iii) estimate, based on the estimated motion of the body-surface patches, a distance between the pacing electrode and the phrenic nerve, and (iv) send an output derived from the estimated distance to the output device.

18 Claims, 2 Drawing Sheets

(51) Int. Cl.
  *A61N 1/05*    (2006.01)
  *A61B 5/06*    (2006.01)
  *A61B 17/00*   (2006.01)
  *A61B 18/00*   (2006.01)

(52) U.S. Cl.
  CPC ............... *A61B 2018/00613* (2013.01); *A61B 2018/00839* (2013.01); *A61B 2018/00898* (2013.01)

(56) References Cited

U.S. PATENT DOCUMENTS

| | | |
|---|---|---|
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 6,772,008 B2 | 8/2004 | Zhu |
| 8,456,182 B2 | 6/2013 | Bar-Tal |
| 8,626,292 B2 | 1/2014 | McCabe |
| 8,649,866 B2 | 2/2014 | Brooke |
| 8,795,188 B2 | 8/2014 | Maschke |
| 9,037,239 B2 | 5/2015 | Brooke |
| 9,776,009 B2 | 10/2017 | Ghosh |
| 2002/0065455 A1 | 5/2002 | Ben Haim |
| 2003/0120150 A1 | 6/2003 | Govari |
| 2004/0068178 A1 | 4/2004 | Govari |
| 2006/0241711 A1 | 10/2006 | Sathaye |
| 2009/0210024 A1 | 8/2009 | M. |
| 2013/0109994 A1 | 5/2013 | Cho |
| 2015/0141798 A1 | 5/2015 | Bar-Tal |
| 2018/0344244 A1 | 12/2018 | Botzer |
| 2020/0077938 A1 | 3/2020 | Jung |

DETECTION AND MAPPING OF PHRENIC NERVE BY PACING

FIELD OF THE INVENTION

The present invention relates generally to invasive medical procedures using medical probes, and particularly to cardiac pacing and ablation procedures.

BACKGROUND OF THE INVENTION

The left and right phrenic nerves, which may be collectively referred to in the singular as "the phrenic nerve," descend from the neck to the diaphragm, passing between the lungs and the heart in close proximity to cardiac tissue. The phrenic nerve is involved in the control of respiration. Undesired movement of the diaphragm due to phrenic irritation (caused as a side effect by cardiac pacing) can trigger spasms in the diaphragm in addition to causing hiccups and breathing difficulties.

Techniques to detect undesired pacing of a phrenic nerve was previously proposed in the patent literature. For example, PCT Application WO 2018/212840 describes a phrenic nerve pacing monitor assembly used during a cryoballoon ablation procedure, which monitors movement of a diaphragm of a patient. The assembly includes a pacing detector and a safety system. The pacing detector directly monitors movement of the diaphragm of the patient to detect when phrenic nerve pacing is occurring. Additionally, the pacing detector generates monitor output based on the movement of the diaphragm of the patient. The safety system receives the monitor output and based at least in part on the monitor output, selectively provides an alert when movement of the diaphragm of the patient is atypical. The safety system is configured to provide the alert only while at least one of (i) phrenic nerve pacing is occurring, and (ii) cryoablation is occurring.

As another example, U.S. Pat. No. 6,772,008 describes a cardiac rhythm management device in which an accelerometer is used to detect diaphragmatic or other skeletal muscle contraction associated with the output of a pacing pulse. Upon detection of diaphragmatic contraction, the device may be configured to automatically adjust the pacing pulse energy and/or pacing configuration.

U.S. Patent Application Publication 2013/0109994 describes systems and methods for monitoring phrenic nerve function of a patient, including establishing a diaphragmatic movement value threshold; positioning a diaphragmatic movement sensor on an external surface of an abdomen of the patient; applying a treatment regimen to a tissue region in proximity to the phrenic nerve; measuring a diaphragmatic movement value with the diaphragmatic movement sensor; comparing the measured diaphragmatic movement value to the established diaphragmatic movement value threshold; and generating an alert in response to the comparison.

SUMMARY OF THE INVENTION

An embodiment of the present invention provides an apparatus including an interface and a processor. The interface is configured to receive one or more magnetic-positioning signals from one or more position sensors coupled to one or more body-surface patches attached to a body of a patient, the magnetic-positioning signals indicative of respective positions of the position sensors. The processor is configured to (i) detect an inadvertent stimulation of a phrenic nerve of the patient, which occurs due to cardiac pacing applied by an intra-cardiac electrode in a heart of the patient, (ii) estimate, based on the magnetic-positioning signals, a motion of one or more of the body-surface patches occurring during the detected stimulation of the phrenic nerve, (iii) estimate, based on the estimated motion of the body-surface patches, a distance between the pacing electrode and the phrenic nerve, and (iv) send an output derived from the estimated distance to the output device.

In some embodiments, the processor is configured to identify that the distance is below a predefined safe limit, and in response output an alert to the output device.

In some embodiments, the processor is configured to estimate the distance by applying a predetermined relation between the estimated motion and the distance.

In an embodiment, the estimated motion includes estimated relative motion of at least two of the position sensors relative to one another. In another embodiment, the estimated motion includes estimated velocity of at least one of the position sensors.

In some embodiments, the estimated motion includes estimated displacement of least one of the position sensors.

In an embodiment, the output includes a warning indicating hazard to the phrenic nerve.

In some embodiments, the processor is configured to identify that the phrenic nerve was stimulated by identifying that a frequency of the estimated motion corresponds to a frequency at which pacing current was applied to the heart. In other embodiments, the processor is further configured to detect an inadvertent stimulation of the phrenic nerve of the patient, which occurs due to cardiac ablation.

In an embodiment, the cardiac ablation method is radiofrequency (RF) ablation and/or Irreversible Electroporation (IRE) and/or Pulse Fielded Ablation (PFA).

There is additionally provided, in accordance with another embodiment of the present invention, a method including receiving one or more magnetic-positioning signals from one or more position sensors coupled to one or more body-surface patches attached to a body of a patient, the magnetic-positioning signals indicative of respective positions of the position sensors. An inadvertent stimulation of a phrenic nerve of the patient is detected, which occurs due to cardiac pacing applied by an intra-cardiac electrode in a heart of the patient. Based on the magnetic-positioning signals, a motion is estimated, of one or more of the body-surface patches occurring during the detected stimulation of the phrenic nerve. Based on the estimated motion of the body-surface patches, a distance is estimated, between the pacing electrode and the phrenic nerve. An output derived from the estimated distance is sent to the output device.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
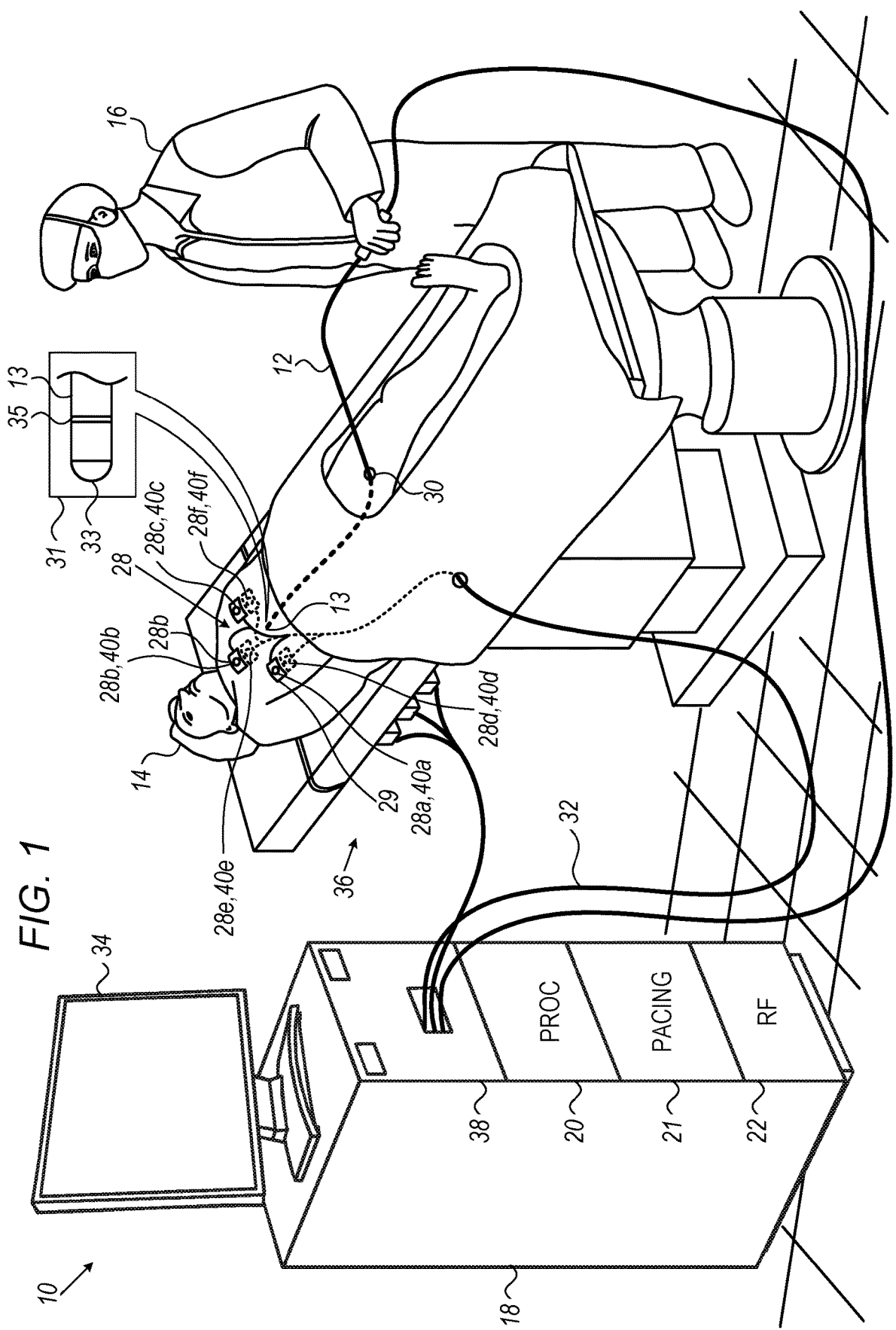
FIG. 1 is a schematic illustration of a system for pacing and ablation of tissue of a patient configured to protect a phrenic nerve of the patient from ablative damage, in accordance with an exemplary embodiment of the present invention.

When performing a cardiac ablation on a patient, it is important to ensure that the phrenic nerve not be damaged by the ablative power, for example, by the nerve tissue being overheated.

Exemplary embodiments of the present invention help prevent damage to the phrenic nerve from ablative power by providing apparatus and methods for accurately estimating a distance between a source of the ablative power (e.g., a catheter electrode) and the phrenic nerve.

In some exemplary embodiments, before performing an ablation, the heart is paced to detect a tissue position to ablate, for example, using a dual-purpose pacing and ablation probe, such as a catheter. A processor measures a resulting electrophysiological activity of the heart, e.g., using the same catheter, and determines if the tissue at the paced position is arrhythmogenic.

To perform a bi-polar pacing, the catheter comprises an electrode pair. In addition to stimulating and sensing of electrophysiological signals, one of the pair electrodes is configured to subsequently ablate tissue site found as arrhythmogenic using ablative electrical power generator to drive the electrode. If unipolar pacing is used, a single catheter electrode may be used for both pacing an ablation.

In some exemplary embodiments, a distance of the ablating electrode from the phrenic nerve is estimated. If the electrode at an arrhythmogenic tissue location, which is identified by the pacing procedure, is determined to be sufficiently distant from the phrenic nerve, the disclosed method enables safe electrical ablation the tissue location with the same electrode used for pacing, so as to accurately treat an arrhythmia.

In some of the disclosed exemplary embodiments, an impedance-based position tracking system is used for measuring the electrode position in the heart, as part of the pacing and ablation procedure. This is done using body-surface patches having electrodes. An example of an impedance-based catheter location-tracking system is the Active Current Location (ACL) system (made by Biosense-Webster, Irvine, Calif.), which applies an impedance-based position-tracking method. With the ACL method, a processor receives position-indicative impedance-magnitudes that are measured between an electrode fitted at a distal end of a catheter and surface electrodes attached to the patient's skin. Based both on the measured impedance-magnitudes and on a stored location-calibrated impedance-magnitudes, the processor of the system estimates a location of the catheter inside an organ of a patient.

In the disclosed exemplary embodiments, one or more of the patches are also fitted with position sensors of a magnetic position-tracking system such as the CARTO™ system, produced by Biosense Webster. During and/or following the passing of each such signal, positions of one or more pairs of patch electrodes, which are coupled to the body of the patient, are measured using magnetic position sensors incorporated into the electrodes. If the pacing current stimulates the phrenic nerve, the breathing of the patient typically begins to quiver, thus causing the measured positions to exhibit relative movement characteristic of a quivering pattern. A processor (i) identifies inadvertent stimulation of the phrenic nerve that occurs due to pacing, and (ii) receives magnetic-positioning signals from the sensors on the patches. Based on these signals, the processor estimates motion of one or more of the patches that occurs during the inadvertent stimulation. From the estimated motion of the patches, the processor estimates the distance between the phrenic nerve and the pacing electrode, and generates a suitable output to the user. A processor is configured to identify this pattern, and, in response thereto, alert the physician that the catheter tip is near the phrenic nerve.

In some exemplary embodiments, the processor analyzes the magnetically measured movement of the patch electrodes during pacing, and using a calibration in a form of a function or table, translates patch motion (e.g., displacement amplitude or velocity) into an electrode-nerve distance. In an embodiment, the processor analyzes an amount of relative movement of the patch electrodes, one against the other, and, using a calibration, estimates a respective distance between the pacing electrode and the phrenic nerve. The measured movement can be used to estimate the distance between the electrode and phrenic nerve by, for example, using a predetermined relation between the movements and such a distance that can be derived offline by calibration.

The processor can compare the estimated distance between the ablation electrode at the arrhythmogenic tissue location and the phrenic nerve to a predetermined minimal safe distance. In case the estimated distance is below a minimal prespecified value (i.e., the distance is below a predefined safe limit), the system may automatically, or the physician may decide to, refrain from ablating the tissue in order to prevent any possible damage to the phrenic nerve. Alternatively, or additionally, the location at which the quivering pattern was identified and quantified may be tagged for a follow-up examination.

In yet another exemplary embodiment, the processor is configured to identify that the phrenic nerve was stimulated by identifying that a frequency of the estimated motion corresponds to a frequency at which the pacing current was passed into the tissue. In a further embodiment, the processor is further configured to detect an inadvertent stimulation of a phrenic nerve of the patient, which occurs due to cardiac ablation. The ablation method may comprise radiofrequency (RF) ablation, Irreversible Electroporation (IRE) and/or Pulse Fielded Ablation (PFA).

By incorporating magnetic position tracking and pacing sensing, the disclosed combined technique may provide accurate information that allows the physician to perform an acutely required cardiac ablative treatment that may otherwise be aborted due to uncertainty regarding a level of hazard to a nearby phrenic nerve.

System Description

FIG. 1 is a schematic illustration of a system 10 for pacing and ablation of tissue of a patient 14 configured to protect a phrenic nerve of the patient from ablative damage, in accordance with exemplary embodiments of the present invention.

System 10 comprises an ablation catheter 12, comprising a distal tip 13 that comprises an ablation electrode 33, seen in inset 31. Electrode 33 is a dual-use electrode, which can be used to apply either unipolar or bi-polar pacing signals with an electrode 35 located just proximally on distal tip 13.

As seen, catheter 12 is inserted by a physician 16 into patient 14. For example, catheter 12 may be inserted, via an insertion point 30, into vasculature of the patient, and may then be navigated, as further described below, to a particular location within the patient's heart. Subsequently, as further described below, catheter 12 is used to ascertain whether the patient's phrenic nerve is located near that particular location. If the phrenic nerve is not nearby, electrode 33 ablates an arrhythmogenic tissue of the patient at the location by passing ablating current into the tissue.

System 10 further comprises a plurality of patch electrodes 28 which are coupled to the body of patient 14. Typically, patch electrodes 28 are coupled to the exterior of the patient's body, e.g., via patches 29 that adhere to the skin of the patient. For example, in the particular embodiment shown in FIG. 1, system 10 comprises six electrodes, one subset of which (patch electrodes 28a, 28b, and 28c) are coupled to chest of the patient, and the other subset (patch electrodes 28d, 28e, and 28f) are coupled to the upper back of the patient, opposite the patient's chest.

Each of patch electrodes 28a-f comprises a respective magnetic position sensors 40a-f. Typically, each such sensor 40a-f comprises a triaxial coil, which generates position-indicative signals in the presence of a magnetic field generated by a magnetic position tracking sub-system of system 10. For that, console 18 further comprises a driver circuit 38, configured to drive magnetic field generators 36.

During pacing of the heart using catheter 12, console 18 receives position signals from sensors 40a-f in response to magnetic fields from external field generators 36. Magnetic field generators 36 are placed at known positions external to patient 14, e.g., below a table on which the patient is lying. These position signals are indicative of the positions of sensors 40a-f in a coordinate system of the magnetic position tracking sub-system. Using the received signals, a processor (PROC) 20 calculates the positions of sensors 40a-f as a function of time.

The method of position and direction sensing using external magnetic fields is implemented in various medical applications, for example, in the aforementioned CARTO™ system, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, which prior applications are hereby incorporated by reference in their entirety herein into this application as if set forth in full.

Using position sensors 40a-f, the exact locations of respective electrodes 28a-f (which changes in time due to the breathing of patient 14) can accurately determine relative motion of electrodes 28a-f at any given time to quantify a breathing pattern of patient 14 while pacing is performed. Using magnetic sensors 40a-f, the different estimated positions can be determined accurately, which therefore improves detection of chest wall displacement as the patient is breathing.

Electrodes 28a-f and respective sensors 40a-f are typically connected via a cable 32 to the console 18, which comprises one or more units that facilitate performance of the techniques described herein. For example, console 18 may comprise processor 20, configured to receive information from the electrodes and the respective sensors, and, based on this information, navigate the catheter as well as check for proximity of the catheter to the phrenic nerve. Console 18 may further comprise a pacing stimulator configured to generate pacing currents, and a radiofrequency (RF) generator 22 configured to generate the RF ablation signals that are passed by electrode 33 of catheter 12 into the patient's tissue.

Figure 2:
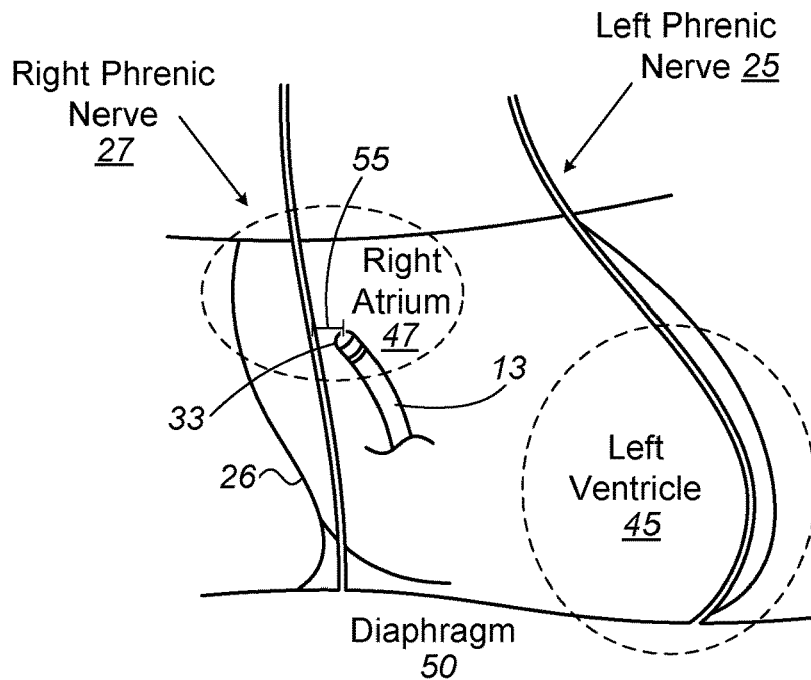
FIG. 2 is schematic illustration of a phrenic nerve separated from a catheter tip by a cardiac chamber wall, in accordance with an exemplary embodiment of the present invention.

Typically, system 10 further comprises a display 34, configured to facilitate performance of the procedure by displaying relevant information to physician 16. For example, processor 20 may show the location of the catheter on display 34, for example, by superimposing an icon representing electrode 33 of the catheter over an image of a patient's anatomy, as schematically shown in FIG. 2. Alternatively or additionally, when processor 20 ascertains that electrode 33 of the catheter is near the phrenic nerve, the processor may alert physician 16 with a suitable warning on display 34.

In some exemplary embodiments, electrodes 28 are used to navigate the catheter within the body of the patient using impedance-based tracking techniques, such as those described in U.S. Pat. No. 8,456,182 and US Patent Application Publication 2015/0141798, whose disclosures are incorporated herein by reference. Such techniques involve repeatedly ascertaining the location of the catheter—in particular, the distal tip thereof—responsively to the different respective impedances exhibited between, for example, electrode 33 of the catheter and each of electrodes 28, and then generating an output that indicates the ascertained location. As described above, such an output may include the display of a relevant icon on display 34 to indicate the current location of the catheter to the physician. Based on this output, the physician may direct the catheter to the desired location.

More specifically, to ascertain the location of electrode 33 at any given time, a current of known amplitude is passed from electrode 33, and the resulting voltages and/or currents are measured at each of electrodes 28. These voltages and currents vary between electrode 33 and electrodes 28, due to the different amount of electrically-impeding tissue between electrode 33 and each of patch electrodes 28. Hence, processor 20 may derive the location of the catheter from the ratios between the measured voltages and/or currents, or between the impedances implied by these voltages and currents.

Advantageously, the same patch electrodes 28 used for navigating the catheter may also be used to ascertain whether electrode 33 of the catheter is near a phrenic nerve, in support of the disclosed magnetic detection technique. A system and method for identifying proximity of a catheter tip to the phrenic nerve using patch electrodes is provided in US Patent Application Publication 2018/0344244, whose disclosures are incorporated herein by reference.

Processor 20 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 20 runs a dedicated algorithm as disclosed herein, including in FIG. 3, which enables processor 20 to perform the disclosed steps, as further described below.

Detection and Mapping of Phrenic Nerve by Pacing

FIG. 2 is schematic illustration of phrenic nerve (25, 27) separated from a catheter tip by a cardiac chamber wall muscle tissue and by the pericardium envelope of the heart, in accordance with an exemplary embodiment of the present invention. As seen, electrode 33 on distal end 13 is located inside the cardiac chamber (e.g., right atrium 47) at a distance 55 from right phrenic nerve 27, passing just outside heart 26. A similar situation may arise if the catheter is inserted into left ventricle 45 and brought to a wall tissue location close to left phrenic nerve 25.

Distance 55 is on the order of the thickness of the myocardium wall muscle plus an additional thickness of the pericardium space and envelope, which may be as small as several millimeters. Performing ablation at either cardiac chamber location without prior estimation of a distance, such as distance 55, may harm the relevant phrenic nerve and may result in serious breathing disruption to the patient, e.g., due to improper neural signaling to diaphragm 50.

Therefore, the disclosed in-situ estimation of distance 55 in real time, and comparison of that distance to a minimal prespecified safe distance, may be crucial to avoid damage to phrenic nerves during cardiac ablation using electrode 33.

The example illustration shown in FIG. 2 is chosen purely for the sake of conceptual clarity, whereas actual anatomy typically varies from patient to patient.

Figure 3:
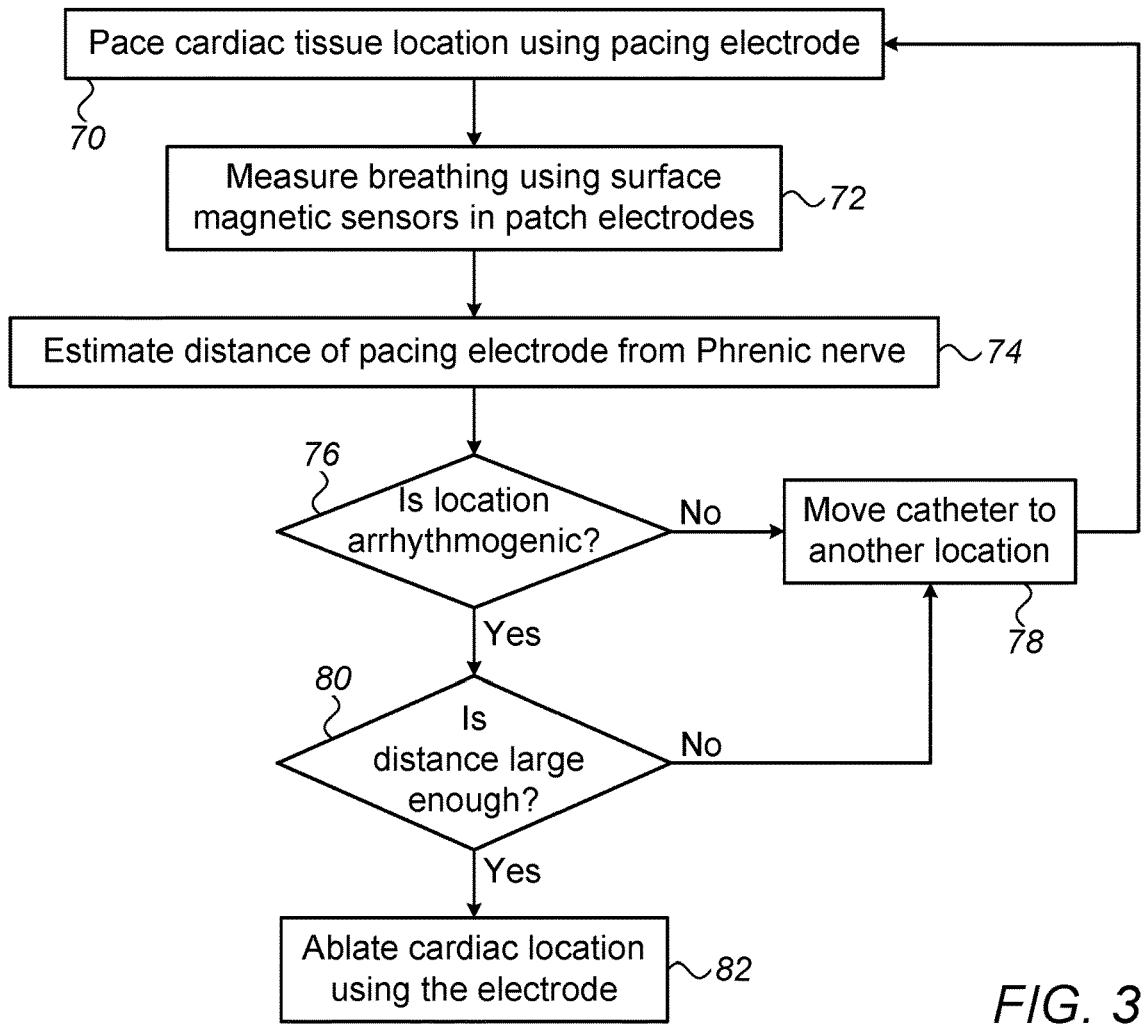
FIG. 3 is a flow chart that schematically illustrates a method for estimating distance of a pacing and ablation electrode of a catheter to a phrenic nerve prior to ablating cardiac tissue, in accordance with an exemplary embodiment of the present invention.

FIG. 3 is a flow chart that schematically illustrates a method for estimating distance 55 of pacing and ablation electrode 33 of catheter 12 to a phrenic nerve (25, 27) prior to ablating cardiac tissue, in accordance with an exemplary embodiment of the present invention. The algorithm, according to the presented embodiment, carries out a process that begins with physician 16 pacing a particular cardiac location inside heart 26 using, for example, electrode 33 to apply unipolar pacing signals to tissue, at a pacing step 70.

At a breath pattern measurement step 72, processor 20 measures a resulting breath pattern (e.g., as manifested by a motion of one or more of the body-surface patches) using position signals from magnetic sensors 40*a-f* inside patch electrodes 28, as described above. Next, using a calibration between the measured breathing pattern (e.g., inter-electrode movement) and an electrode-nerve distance, processor 40 estimates a distance 55 between pacing electrode 33 and a phrenic nerve, at a distance estimation step 74.

If, at an arrhythmia diagnostic step 76, the paced location is deemed by the physician, or by a processor, to be a normal tissue location, i.e., which does not require treatment, the physician continues pacing by moving the catheter to another location, at a catheter moving step 78. The process then returns to pacing step 70.

If, on the other hand, the location is determined to be arrhythmogenic tissue, the processor compares distance 55 to the minimal prespecified safe distance, at a distance checking step 80. If estimated distance 55 is determined to be large enough (i.e., above a predefined safe limit), the physician ablates tissue at the location using the same electrode used for pacing at step 82.

The example flow chart shown in FIG. 3 is chosen purely for the sake of conceptual clarity. In alternative embodiments, for example, bipolar pacing signals may be applied between electrodes 33 and 35. In a pacing procedure, an additional reference signal sensing catheter (not shown) may be inserted and placed inside the coronary sinus of heart 26.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for identifying proximity of an ablation catheter to a phrenic nerve of a patient's heart, comprising:
   an interface, configured to receive magnetic-positioning signals from a first pair of position sensors, each coupled to a patch attached to a patient's skin and a second position sensor coupled to the catheter, the magnetic-positioning signals indicative of respective positions of the position sensors; and
   a pacing stimulator configured direct current to an electrode of the catheter for delivering a pacing signal to a pacing location;
   a processor, configured to:
      identify a pattern of the motion indicative of phrenic nerve stimulation due to pacing based on the magnetic-positioning signals from the first pair of position sensors; and
      estimate distance between the pacing location and the phrenic nerve based on the identified pattern and the magnetic-positioning signals from the second position sensor;
      prior to delivering an ablation signal at a selected location, determine if the selected location is within a predefined distance from the phrenic nerve based on the selected location, the pacing location and the distance estimated; and
   a display configured to initiate a warning not to ablate at the selected location, based on determining that the selected location is within the predefined distance.

2. The apparatus according to claim 1, wherein the estimated motion comprises estimated relative motion of the first pair of position sensors relative to one another.

3. The apparatus according to claim 1, wherein the estimated motion comprises estimated velocity of the first pair of position sensors.

4. The apparatus according to claim 1, wherein the estimated motion comprises estimated displacement of the first pair of position sensors.

5. The apparatus according to claim 1, wherein the processor is configured to identify that the phrenic nerve was stimulated by identifying that a frequency of the estimated motion corresponds to a frequency at which pacing current was applied to the heart.

6. The apparatus according to claim 1, wherein the processor is further configured to detect an inadvertent stimulation of the phrenic nerve of the patient, which occurs due to cardiac ablation.

7. The apparatus according to claim 6, wherein the cardiac ablation is selected to be one or more of radiofrequency (RF) ablation, Irreversible Electroporation (IRE) and Pulse Fielded Ablation (PFA).

8. The apparatus of claim 1, wherein the display is configured to render an image of portion of the patient's heart and to track positions of the electrode within the patient's heart.

9. The apparatus of claim 1, wherein the display is configured to display a tag on the rendered image at the pacing location that provided the pattern of the motion indicative of phrenic nerve stimulation.

10. A method for identifying proximity of an ablation catheter to a phrenic nerve of a patient's heart, the method comprising:
   receiving magnetic-positioning signals from a first pair of position sensors, each coupled to a patch attached to a patient's skin and a second position sensor coupled to the catheter, the magnetic-positioning signals indicative of respective positions of the position sensors; and delivering a pacing signal to a pacing location with an electrode of the catheter;

identifying a pattern of the motion indicative of phrenic nerve stimulation due to pacing based on the magnetic-positioning signals from the first pair of position sensors; and estimating a distance between the pacing location and the phrenic nerve based on the identified pattern and the magnetic-positioning signals from the second position sensor;

prior to delivering an ablation signal at a selected location, determining if the selected location is within a predefined distance from the phrenic nerve based on the selected location, the pacing location and the distance estimated; and displaying a warning not to ablate at the selected location, based on determining that the selected location is within the predefined distance.

11. The method according to claim 10, wherein estimating the motion comprises estimating relative motion of the first pair of position sensors relative to one another.

12. The method according to claim 10, wherein estimating the motion comprises estimating velocity of first pair of position sensors.

13. The method according to claim 10, wherein estimating the motion comprises estimating displacement of the first pair of position sensors.

14. The method according to claim 10, wherein identifying that the phrenic nerve was stimulated comprises identifying that a frequency of the estimated motion corresponds to a frequency at which pacing current was applied to the heart.

15. The method according to claim 10, and comprising detecting an inadvertent stimulation of the phrenic nerve of the patient, which occurs due to cardiac ablation.

16. The method according to claim 15, wherein the cardiac ablation comprises one of radiofrequency (RF) ablation, Irreversible Electroporation (IRE) and Pulse Fielded Ablation (PFA).

17. The method of claim 10, rendering in image of portion of the patient's heart and tracking positions of the electrode on the rendered mage.

18. The apparatus of claim 17, displaying a tag on the rendered image at the pacing location that provided the pattern of the motion indicative of phrenic nerve stimulation.

* * * * *